(12) United States Patent
Haggerty (10) Patent No.: US 11,604,126 B2
(45) Date of Patent: Mar. 14, 2023

(54) DETERMINING WHEN APPLIED STRESS TO A CORE ROCK SAMPLE HAS EQUILIBRATED IN THE CORE ROCK SAMPLE

(71) Applicant: Halliburton Energy Services, Inc., Houston, TX (US)

(72) Inventor: Dennis J. Haggerty, Burleson, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 832 days.

(21) Appl. No.: 16/497,312

(22) PCT Filed: Dec. 18, 2018

(86) PCT No.: PCT/US2018/066280
§ 371 (c)(1),
(2) Date: Sep. 24, 2019

(87) PCT Pub. No.: WO2020/131039
PCT Pub. Date: Jun. 25, 2020

(65) Prior Publication Data
US 2021/0131931 A1    May 6, 2021

(51) Int. Cl.
*G01N 3/10* (2006.01)
*E21B 49/02* (2006.01)
(Continued)

(52) U.S. Cl.
CPC .............. *G01N 3/10* (2013.01); *E21B 49/02* (2013.01); *G01N 15/0826* (2013.01);
(Continued)

(58) Field of Classification Search
CPC .......... G01V 1/30; G01V 1/32; G01N 15/088; G01N 3/10; G01N 15/0826; G01N 33/24;
(Continued)

(56) References Cited

U.S. PATENT DOCUMENTS 5,282,384 A * 2/1994 Holbrook ................ E21B 21/08
                                                        73/382 R
6,374,186 B1 * 4/2002 Dvorkin ................. G01V 1/284
                                                        367/75
(Continued)

FOREIGN PATENT DOCUMENTS

CN    102353625 A  *  2/2012
CN    106153518 B     11/2016
(Continued)

OTHER PUBLICATIONS

PCT Application Serial No. PCT/US2018/066280, International Search Report, dated Sep. 18, 2019, 3 pages.
(Continued)

*Primary Examiner* — Octavia Davis Hollington
(74) *Attorney, Agent, or Firm* — Delizio, Peacock, Lewin & Guerra (57) ABSTRACT

Overburden stress is applied to a core rock sample in a sleeve. Pressure is applied to pores in the core rock sample. An overburden fluid pressure indicative of the overburden stress and pore fluid pressure indicative of the pore pressure is measured. A difference between the overburden fluid pressure and pore fluid pressure is determined. The measuring and determination of the difference is repeated over a period of time. A rate of change of the difference over the period of time is determined. An indication of the rate of change meeting a threshold level is output indicative of the overburden stress transferring into and throughout the core rock sample.

18 Claims, 7 Drawing Sheets

(51) Int. Cl.
*G01N 15/08* (2006.01)
*G01N 33/24* (2006.01)

(52) U.S. Cl.
CPC ..... *G01N 33/24* (2013.01); *G01N 2203/0019* (2013.01); *G01N 2203/0048* (2013.01)

(58) Field of Classification Search
CPC .... G01N 2203/0019; G01N 2203/0048; E21B 49/006; E21B 49/02
USPC ..................................................... 73/152.07
See application file for complete search history.

(56) References Cited

U.S. PATENT DOCUMENTS

| | | | |
|---|---|---|---|
| 6,751,558 B2 * | 6/2004 | Huffman | G01V 1/32 |
| | | | 702/14 |
| 2014/0007667 A1 | 1/2014 | Haggerty | |
| 2014/0122035 A1 | 5/2014 | Dean et al. | |
| 2018/0340417 A1 | 11/2018 | Cooper et al. | |
| 2018/0340878 A1 | 11/2018 | Liu et al. | |
| 2020/0225137 A1 * | 7/2020 | Manning | E21B 49/08 |

FOREIGN PATENT DOCUMENTS

| | | | | | |
|---|---|---|---|---|---|
| CN | 106383221 A | * | 2/2017 | ............. | G01N 33/24 |
| CN | 106960264 A | * | 7/2017 | ............. | G06Q 10/04 |

OTHER PUBLICATIONS

PCT Application Serial No. PCT/US2018/066280, International Written Opinion, dated Sep. 18, 2019, 8 pages.

\* cited by examiner

DETERMINING WHEN APPLIED STRESS TO A CORE ROCK SAMPLE HAS EQUILIBRATED IN THE CORE ROCK SAMPLE

TECHNICAL FIELD

This disclosure generally relates to the field of earth or rock drilling (mining), and more particularly to determining when applied stress on a core rock sample has equilibrated in the core rock sample.

BACKGROUND ART

A perforating gun is inserted downhole in a wellbore drilled in a geologic formation. One or more shaped charges inside the perforating gun are then detonated which causes the casing which lines the wellbore to be perforated and rock beyond the casing to be penetrated creating a perforation tunnel. Hydrocarbons in the rock can then flow through these tunnels, perforations, and into the casing of the wellbore for extraction to the surface.

A depth of the perforation tunnel in the rock typically depends on a compressive strength of the rock and design of the shaped charge. In this regard, the shaped charges need to be tested before being used downhole to determine whether performance downhole will be acceptable. The testing usually occurs at the surface by simulating conditions downhole and then detonating the shaped charges under the simulated conditions. Accurate simulation ensures that the shaped charge will perform as expected downhole.

BRIEF DESCRIPTION OF THE DRAWINGS

Embodiments of the disclosure may be better understood by referencing the accompanying drawings.

The drawings are for purpose of illustrating example embodiments, but it is understood that the inventions are not limited to the arrangements and instrumentalities shown in the drawings.

DESCRIPTION OF EMBODIMENTS

The description that follows includes example systems, methods, techniques, and program flows that embody embodiments of the disclosure. However, it is understood that this disclosure may be practiced without these specific details. For instance, this disclosure refers to determining when applied stress on a core rock sample has equilibrated in the core rock sample in illustrative examples. Embodiments of this disclosure can instead be applied to samples other than core rock samples to simulate conditions other than downhole. In other instances, well-known instruction instances, protocols, structures and techniques have not been shown in detail in order not to obfuscate the description.

Overview

A testing chamber is used to test shaped charges. The testing chamber simulates at the surface conditions downhole to determine whether performance of the shaped charges downhole will be acceptable. The testing chamber includes an overburden chamber and a wellbore chamber.

The overburden chamber simulates overburden stress applied on a core rock sample as if the core rock sample was actually downhole. The core rock sample is placed in a vessel of the overburden chamber. The core rock sample further saturated with a pore fluid such as brine, mineral oil, lab oil, or kerosene prior to being placed in the vessel. To contain the pore fluid, a rubber sleeve is placed around the core rock sample. The vessel fills with overburden fluid under pressure, e.g., water around the core rock sample, which in turn applies a stress around sleeve of the core rock sample resulting in the sleeve compressing and squeezing the core rock sample within confines of the vessel. The applied stress is indicative of stress imposed on the core rock sample by weight of overlying material (soil and/or rock) if the core rock sample was actually downhole, commonly known as overburden stress. As the overburden stress is applied and the rock compresses, the pore fluid in the core rock sample is forced out of the core rock sample through tubing running through the overburden chamber. A pore pump will apply a pore fluid pressure to the pore fluid in the tubing which produces a pore pressure within a rock's pore space also indicative of conditions downhole.

The shaped charge is typically positioned downhole to perforate a casing and cement behind the casing downhole in addition to the rock. To simulate this perforation process at the surface, a portion of a casing to be perforated downhole and/or cement which would be behind this casing are placed against the core rock sample in the overburden chamber. Also, the shaped charge under test is placed in a perforation gun which is then positioned in the wellbore chamber near the casing. The wellbore chamber simulates conditions in the casing of the wellbore by applying a pressure indicative of a wellbore pressure on the perforation gun. For example, the perforation gun (which is sealed) is placed in a vessel of the wellbore chamber and a wellbore fluid pressurized to a wellbore fluid pressure applies pressure on the perforation gun similar to how the overburden fluid pressurized to the overburden fluid pressure applies pressure on the core rock sample.

The overburden fluid pressure, pore fluid pressure, and wellbore fluid pressure are indicative of overburden stress applied to the core rock sample, pore pressure in the rock's pore space, and wellbore pressure in the wellbore respectively. The pressures are increased to respective target pressures indicative of conditions downhole. Upon the respective target pressures being reached, the perforation gun detonates the shaped charge under test in the wellbore chamber. The core rock sample is then analyzed to evaluate perforations that are formed and the perforation tunnels created in the core rock sample by the shaped charges.

Different core rock samples will have different rock properties. As a result, different times are required for the overburden stress applied on the core rock sample to transfer into and throughout the core rock sample sufficient for testing of the shaped charges. A rock will compress when the overburden stress is applied. The overburden stress is considered transferred into and throughout the core rock sample when the core rock sample stops compressing. This time depends on the compressive strength of the rock. The higher the compressive strength of the core rock sample, the longer the time for rock to stop compressing, i.e., the core rock sample has a higher resistance to stressing. Conversely, the lower the compressive strength of the core rock sample, the faster the time for the rock to stop compressing, i.e., the core rock sample has a lower resistance to stressing. When the rock stops compressing, an equilibrium is reached. The overburden stress applied on the core rock sample by the overburden chamber has transferred into and throughout the core rock sample. In this regard, determining that one or more of the overburden fluid pressure, pore fluid pressure, and wellbore fluid pressure meet respective target pressures might not be indicative of whether overburden stress applied on the core rock sample has transferred into and throughout the core rock sample sufficient for testing of the shaped charges.

Embodiments described herein are directed to determining whether overburden stress applied on the core rock sample has transferred into and throughout the core rock sample. A pressure transducer has two inputs, one input which is coupled to tubing which carries the overburden fluid and another input which is coupled to tubing which carries the pore fluid. The pressure transducer is used to determine a difference between pore fluid pressure and overburden fluid pressure which is provided to a data acquisition system. The data acquisition system monitors this difference over time and calculates a rate of change of this difference over time. The rate of change is indicative of whether the core rock sample has stopped compressing. If the rate of change varies by less than a threshold amount, e.g. 0.1% per minute, then the core rock sample is no longer compressing. The overburden stress applied on the core rock sample has transferred into and throughout the core rock sample, equilibrated in the core rock sample, and any transient behavior is due to thermal effects. Upon reaching this condition, an indication such as audible sound or light is provided. In response the indication, the shaped charge in the perforation gun is detonated to simulate how the shaped charge will perform downhole.

The description that follows includes example systems, apparatuses, and methods that embody aspects of the disclosure. However, it is understood that this disclosure may be practiced without these specific details. In other instances, well-known instruction instances, structures and techniques have not been shown in detail in order not to obfuscate the description.

Example Illustration

A wellbore is drilled in a geologic formation to facilitate extraction of hydrocarbons from a reservoir in the geologic formation. The wellbore is typically lined with a casing such as steel pipe cemented in place in the wellbore. The casing serves multiple purposes. The casing prevents the wellbore from caving in, keeps hydrocarbon carried within the casing from escaping out of the casing, and prevents unwanted fluids such as water outside of the casing from entering into the casing and contaminating the hydrocarbon carried within the casing.

Certain regions of the casing are perforated to allow hydrocarbon to flow from the reservoir into the casing. To perforate the casing, a perforation gun having shaped charges is positioned downhole. The shaped charges are explosive devices that utilizes a cavity-effect explosive reaction to generate a high-pressure, high-velocity jet that creates a perforation tunnel. The extremely high pressure and velocity of the jet cause materials, such as steel, cement and rock formations, to flow plastically around a jet path. In this regard, the shaped charges not only perforate the casing but also produces perforation tunnels in rock. Hydrocarbons in the rock can then flow through these perforation tunnels and perforations into the casing of wellbore for extraction.

Figure 1:
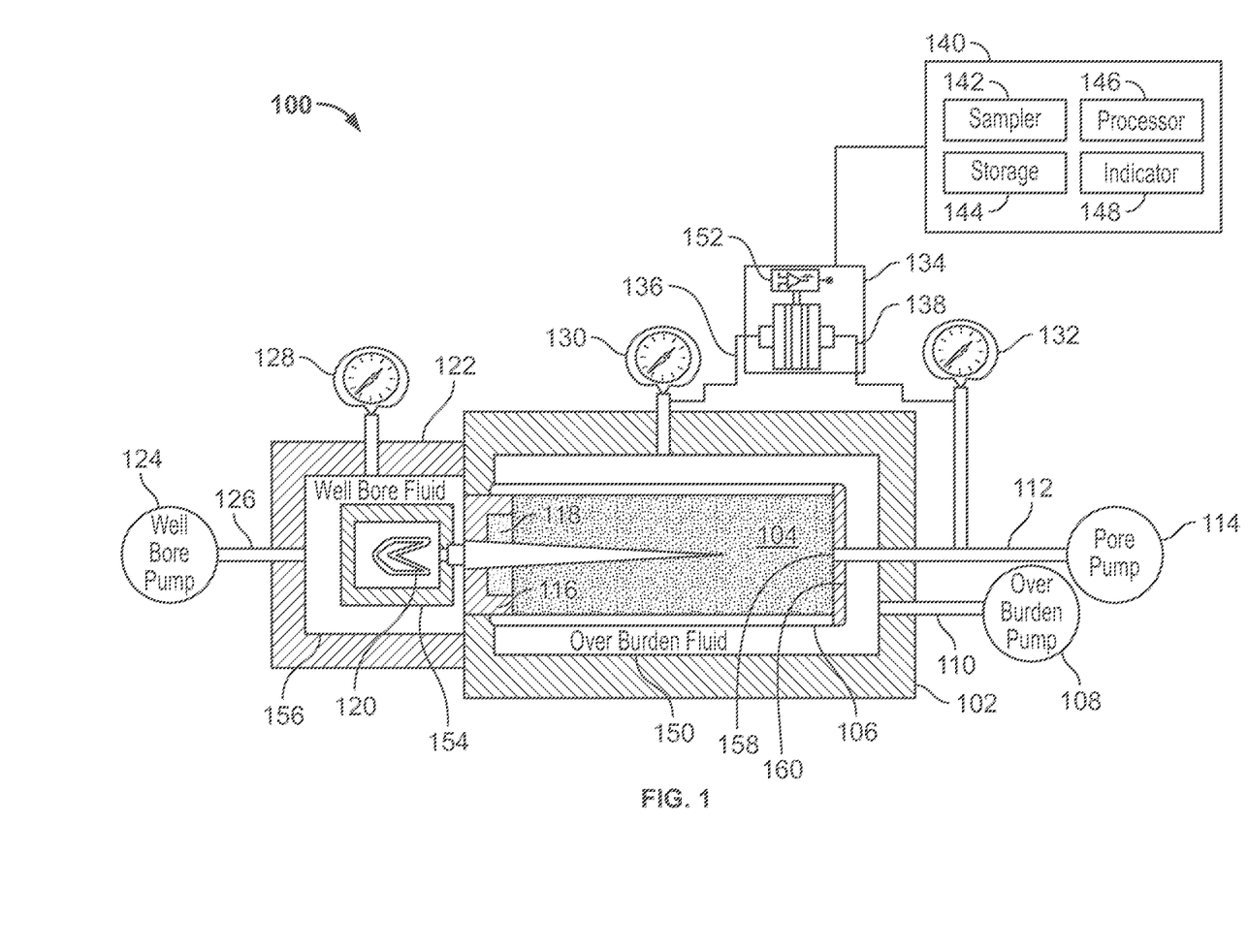
FIG. 1 illustrates a testing arrangement for testing shaped charges prior to being used downhole.

FIG. 1 illustrates a testing chamber 100 for testing shaped charges prior to being used downhole. The testing chamber 100 includes an overburden chamber 102 and a wellbore chamber 122. The testing chamber 100 simulates at the surface conditions downhole. Accurate simulation ensures that the shaped charge will perform as expected downhole.

A core rock sample 104 representing porous rock to be perforated downhole is placed in a vessel 150 of the overburden chamber 102 for purposes of the testing. The core rock sample 104 may be appropriately sized to enable perforation testing of the shaped charges. For example, the core rock sample 104 may be a cylindrical core rock sample having a radius of four or seven inches and longitudinal length between 12 to 27 inches depending on the shaped charge under test. The core rock sample 104 may be the same type of rock found downhole in a reservoir such as Indiana sandstone, shale, or Berea sandstone.

The core rock sample 104 may be saturated with a pore fluid via a saturation process prior to being placed in the overburden chamber 102. The saturation process may include drying out the core rock sample 104 by placing it in an oven which heats the core rock sample 104 to a predefined temperature such as 200 to 210 degrees Fahrenheit. At predefined intervals, the core rock sample 104 may be weighed to determine its weight and placed back in the oven. When the weight does not change or does not change by a predefined amount over the predefined intervals, then the core rock sample 104 may be ready for saturation with a pore fluid such as 3% by weight sodium chloride brine, lab oil, mineral oil, or kerosene. The core rock sample 104 may be placed in a container of the pore fluid such that the core rock sample 104 may wick the pore fluid. The core rock sample 104 may be considered saturated when a difference between a weight of the core rock sample before and after wicking reaches a threshold level.

The overburden chamber 102 may have a sleeve 106 positioned around at least a portion of the core rock sample 104 to contain the pore fluid. For example, the sleeve 106 may be a rubber sleeve wrapped around a circumference of the core rock sample. The overburden pump 108 may pump the overburden fluid, e.g., water under pressure, into the vessel 150 and around the sleeve 106 resulting in the sleeve 106 compressing and squeezing the core rock sample 104 within confines of the vessel 150. As the core rock sample 104 is squeezed, the pore fluid in the core rock sample 104 may be pushed out of the core rock sample 104. The sleeve 106, being an impermeable membrane, results in the pore fluid exiting a port 158 of an end plate 160 of the core rock sample 104 and into tubing 112 coupled to a pore pump 114. The pore pump 114 may apply a pressure to the pore fluid to produce a pore pressure indicative of pressure exerted by the pore fluid within a rock's pore space.

A portion of casing 116 representative of downhole casing is placed in the overburden chamber 106 and positioned against the core rock sample 104 in the overburden chamber 106. The downhole casing positioned in an actual wellbore may be a cylindrical steel pipe, but the portion of the casing 116 for simulation purposes may be either a curved with a radius similar to the downhole casing or planar. Experiments show that a size of the perforations generated by shaped charges in planar and curved casing differ by less than 5%, resulting in curved or planar casings being interchangeable. A cement block 118 may also be placed behind the casing 116. The cement block 118 may be indicative of cement which fills an annulus between the casing and wellbore downhole.

The wellbore chamber 122 may have a vessel 156 and a perforation gun 154 inside the vessel 156. The perforation gun 154 may have a shaped charge 120 positioned near the casing 116. In one or more examples, the perforation gun 154 may be in a dry sealed cylindrical housing which houses the shaped charge 120 and simulates a gun housing. The shaped charge 120 may have a blasting cap which ignites explosives when the perforation gun detonates the shaped charge 120 in the wellbore chamber 104. A shape of the explosive material and powdered metal lining in the shaped charge 120 determines the shape of the jet and performance characteristics of the charge. The wellbore chamber 104 may produce a pressure on the perforation gun 154 indicative of pressure in the wellbore as if the perforation gun 154 was actually downhole. The pressure may be produced in a manner similar to the pressure produced by the overburden stress. For example, a wellbore pump 124 may pump wellbore fluid, e.g., water under pressure into the vessel 156, via tubing 126, around the perforation gun 154, squeezing the perforation gun 154.

The testing chamber 100 may have a wellbore fluid pressure gauge 128, an overburden fluid pressure gauge 130, a pore fluid pressure gauge 132, and a pressure transducer 134. The wellbore fluid pressure gauge 128 may receive the wellbore fluid which is pressurized in the vessel 156 and output an indication of the wellbore fluid pressure. The overburden fluid pressure gauge 130 may receive the overburden fluid which is pressurized in the vessel 150 and output an indication of the overburden fluid pressure. The pore fluid pressure gauge 132 may receive the pore fluid which is pressurized at the pore fluid pressure and output an indication of the pore fluid pressure.

The pressure transducer 134 may measure a pressure difference between the overburden fluid and the pore fluid. The pressure transducer 134 may have two inputs 136, 138, one input 136 which receives the overburden fluid which is pressurized in the vessel 150 and the other input 138 which receives the pore fluid from the tubing 112 which is pressurized at the pore fluid pressure. The pressure transducer 134 may measure the pressures. For example, the pressure transducer may sense each pressure and convert it into an electric signal where the amount depends upon the pressure applied. In one or more examples, the pressure transducer may also output a difference between the pressures of the overburden fluid and pore fluid in which case the pressure transducer 134 is a differential pressure transducer. The difference may be output by a comparator 152 which compares the overburden fluid pressure and pore fluid pressure.

A data acquisition system 140 may receive the output of the pressure transducer 134. The data acquisition system 140 may be directly coupled to the pressure transducer 134 or coupled via a wired or wireless communication network (not shown). The data acquisition system 140 may have a sampler 142, storage 144, processor 146, and indicator 148. The sampler 142 may electronically sample the output of the pressure transducer 134 at a defined rate (e.g., continuously or discretely). The storage 144 may store an indication of the sampled output. The storage 144 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.). The processor 146 may include one or more of hardware and/or software for processing the sampled output. The indicator 148 may produce an audible indication such as a beep and/or visual indication such as a flashing or continuous light based on this processing indicative of the shaped charge 120 being ready for detonation.

Different core rock samples will have different rock properties. As a result, different times are required for the overburden stress applied on the core rock sample by the overburden chamber to transfer into and throughout the core rock sample sufficient for testing of the shaped charges. A rock will compress when the overburden stress is applied. The overburden stress is considered transferred into and throughout the core rock sample when the core rock sample stops compressing. This time depends on the compressive strength of the rock. The higher the compressive strength of the core rock sample, the longer the time to stop compressing, i.e., the core rock sample has a higher resistance to stressing. Conversely, the lower the compressive strength of the core rock sample, the faster the time to stop compressing, i.e., the core rock sample has a lower resistance to stressing. When the rock stops compressing, an equilibrium is reached. The overburden stress applied on the core rock sample by the overburden chamber has transferred into and throughout the core rock sample.

Figure 2:
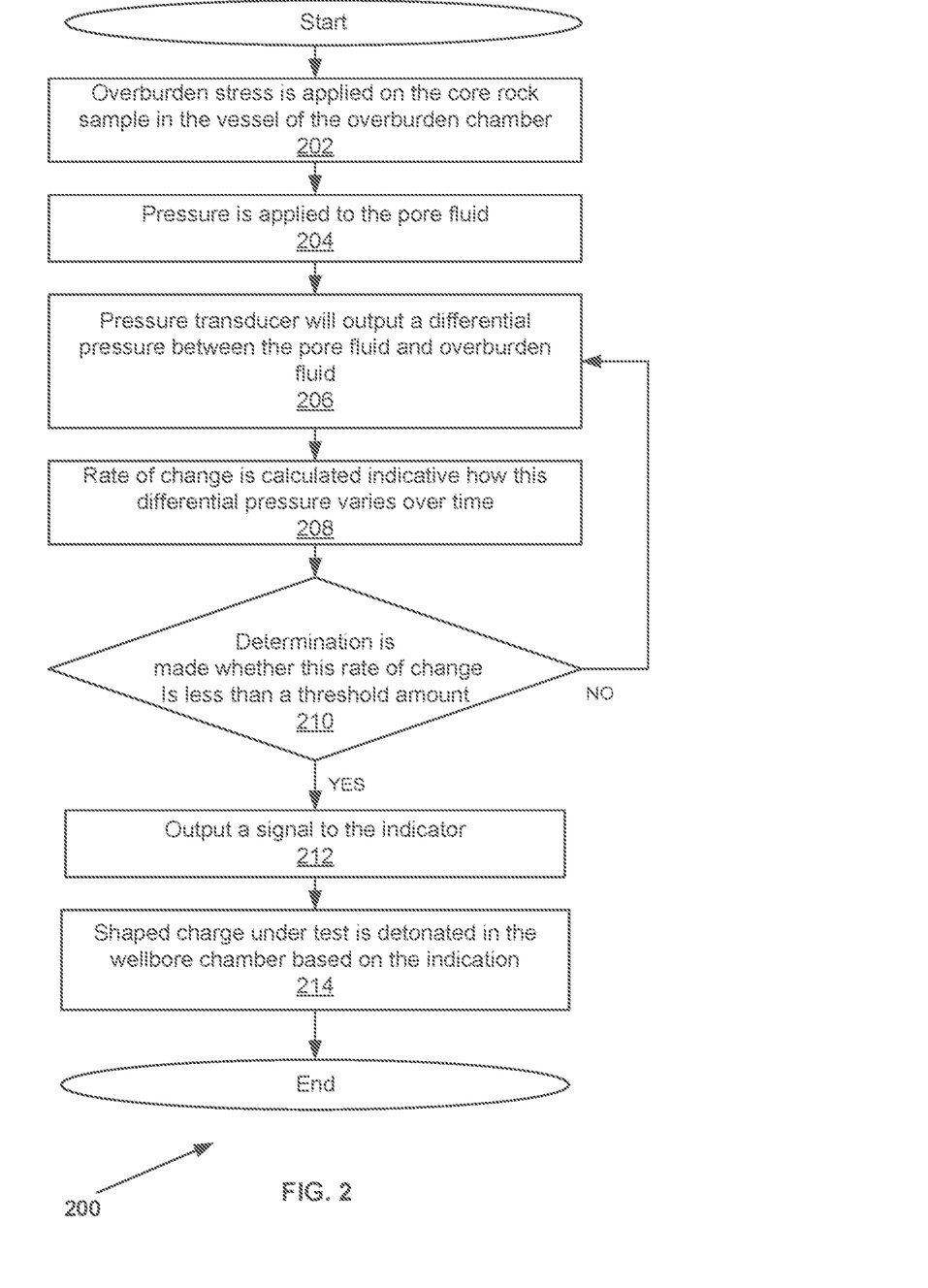
FIG. 2 is a flow chart of functions for determining when applied stress to a core rock sample has equilibrated in the core rock sample.

FIG. 2 is a flow chart 200 of functions associated with the testing chamber arranged with the pressure transducer. The pressure transducer indicates whether the stress applied on the core rock sample has transferred into and throughout the core rock sample rather than making an assumption based on one or more of the overburden fluid pressure, pore fluid pressure, and wellbore pressure meeting respective target pressures. The transfer of stress will indicate that the shaped charge is ready for detonation in the wellbore chamber.

At 202, overburden stress is applied on the core rock sample in the vessel of the overburden chamber. The overburden pump may pump the overburden fluid, e.g., water under pressure, into the vessel and around the sleeve of the core rock sample resulting in the sleeve compressing and squeezing the core rock sample within confines of the vessel. The overburden stress is indicative of stress on the core rock sample imposed by the weight of overlying soil or rock if the core rock sample was actually downhole. The overburden fluid may be pumped into the vessel until the overburden fluid pressure gauge indicates that the overburden fluid pressure reaches a given amount over a given period of time at which point the pumping may stop. The overburden fluid pressure may be indicative of the overburden stress. The given amount of pressure may be 10,000 pounds per square inch (psi) or some other pressure.

At 204, pressure is applied to the pore fluid inside the pore space in the core rock sample. As the core rock sample is squeezed, the pore fluid in the core rock sample may be pushed out of the core rock sample. Further, the sleeve of the core rock sample directs the pore fluid into tubing coupled to a pore pump. The pore pump applies a given amount of pressure to the pore fluid to produce a pore fluid pressure indicative of pore pressure within a rock's pore space. The given amount of pressure may be 8,000 psi or some other pressure. The pore pump may be pumped until the pore fluid pressure gauge indicates that the pore fluid pressure reaches a given amount over a given period of time, at which point the pumping may stop.

At 206, the pressure transducer in the form of the differential pressure transducer outputs a differential pressure between the pore fluid and overburden fluid. The differential pressure may be provided to the data acquisition system.

At 208, a rate of change is calculated indicative how this differential pressure varies over time. The sampler may sample the differential pressures at a fixed or variable interval of time and store an indication of the sampled differential pressures in the storage. The processor may then calculate a difference of the differential pressures over time indicative of the rate of change. For example, the rate of change may be the difference between the differential pressure at time T and time T+n, where n is a time between samples, divided by time interval n. An indication of the rate of change may be stored in the storage. The rate of change is indicative of whether the core rock sample has stopped compressing.

At 210, a determination is made whether this rate of change is less than a threshold amount, e.g. 0.1% per minute. If the rate of change is less than the threshold, then the overburden stress applied on the core rock sample has transferred into and throughout the core rock sample and any transient behavior is due to thermal effects. Otherwise, processing returns back to step 206 because the core rock sample is still compressing. The overburden stress applied on the core rock sample has not transferred into and throughout the core rock sample such that equilibrium is reached.

At 212, the processor may output a signal to an indicator when the rate of change is less than the threshold. The indicator may provide an indication such as audible sound or light which indicates that equilibrium has been reached.

At 214, the shaped charge in the wellbore chamber is detonated based on the indication. The wellbore chamber may have a perforation gun with a shaped charge under test. To simulate wellbore conditions, the wellbore pump may pump wellbore fluid, e.g., water under pressure, via tubing into the wellbore chamber around the perforation gun, squeezing the perforation gun similar to how overburden stress is applied by the overburden fluid to the core rock sample. The wellbore fluid may produce a target wellbore pressure around the perforation gun indicative of conditions downhole. In turn, the detonation simulates how the shaped charge will performed downhole when the overburden stress applied on the core rock sample has transferred into and throughout the core rock sample. The core rock sample is then analyzed to evaluate penetration of the core rock sample by the shaped charges and the perforations that are formed if the core rock sample was actually downhole.

Figure 3:
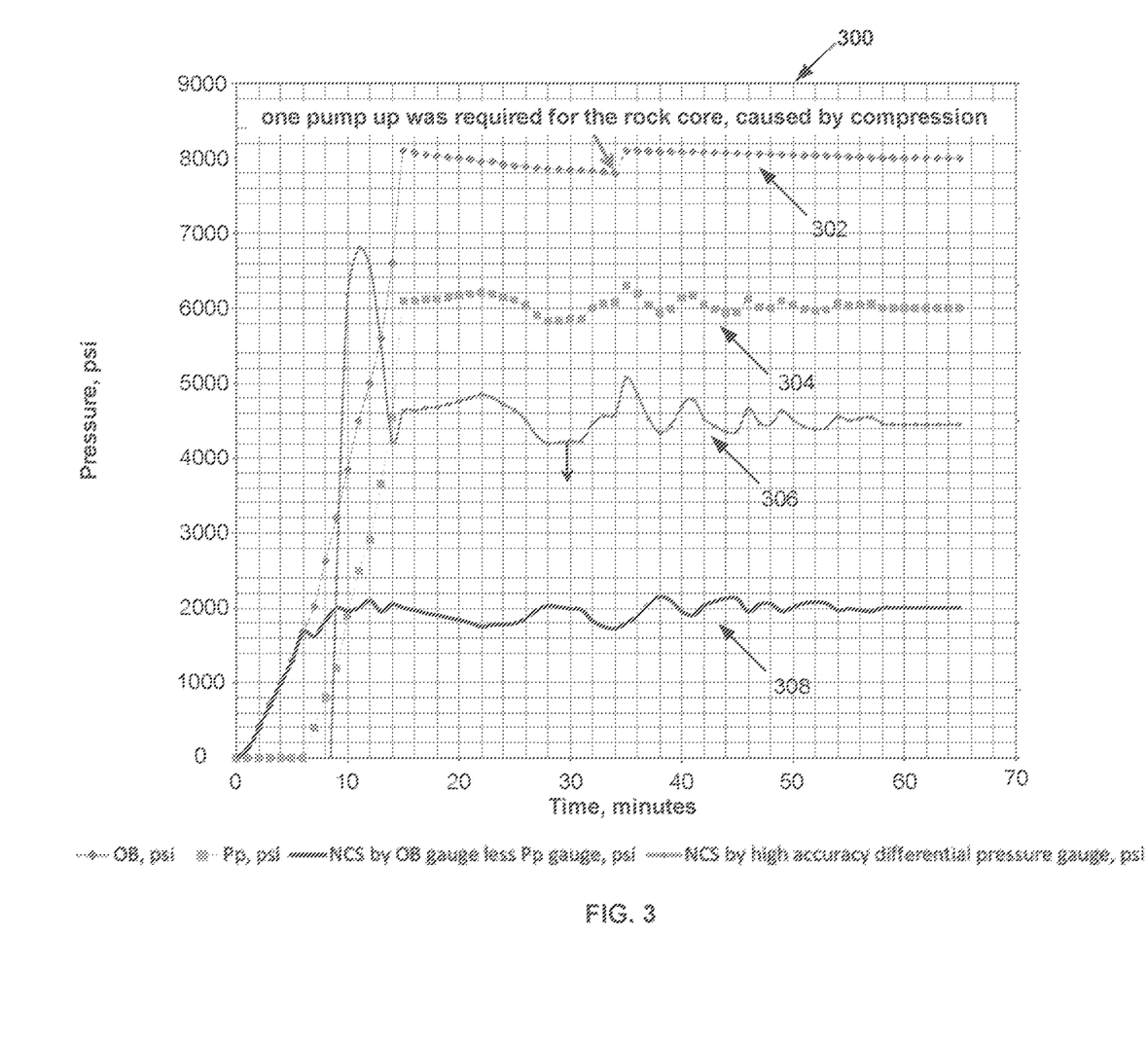
FIG. 3 is an example of a transient pressure chart.

FIG. 3 is an example of a transient pressure chart 300. The transient pressure chart 300 shows pressures curves based on measurements by the various gauges associated with the testing chamber and the differential pressure transducer over time. The pressure curves shown include the overburden (OB) pressure curve 302 measured by the overburden pressure gauge, the pore fluid pressure (Pp) curve 304 measured by the pore fluid pressure gauge, the differential pressure curve 306 (referred to as a net confining stress (NCS) or effective stress in a subsurface formation) measured by the differential pressure transducer, and the net pressure curve 308 (NCS) calculated as a difference between the OB and Pp, measured over time. The overburden pump and pore pump may pump overburden fluid and pore fluid respectively until respective pressures remain at a given level for a given period of time. If needed, a pump may increase pressure due to compression of the core rock sample as shown by the OB pressure curve 302. At some point, e.g., 62 minutes, it can be assumed that enough time has elapsed for the overburden stress applied on the core rock sample to transfer into and throughout the core rock sample at which point the shaped charge may be detonated. An indication that sufficient time has passed may be the differential pressure remaining constant for a given period of time or consistently decreasing (provided no leaks exist in the sleeve).

The overburden stress is applied to the core rock sample and the pore pressure is applied within the pores of the core rock sample in a variety of ways. For example, the overburden stress and pore pressure may be increased while setting a limit on the net difference between the two. Once the target overburden stress and pore pressure are reached, the pressure transducer will monitor the differential pressure between the pore fluid and overburden fluid. In one illustration, if downhole conditions to match has 10,000 psi overburden fluid pressure and 6,000 psi pore fluid pressure, the net is 4,000 psi. Overburden fluid pressure is increased to approximately 3,000 psi before pore fluid pressure is increased. Then, the overburden fluid pressure and pore fluid pressure are raised simultaneously to maintain a 3,000 psi differential until 10,000 psi overburden fluid pressure and 7,000 psi pore fluid pressure is reached. Then pore fluid pressure is dropped to 6,000 psi pore pressure while maintaining the 10,000 psi on the overburden fluid pressure. The core rock sample is not overstressed at any time, e.g., 10,000 psi overburden fluid pressure and 5,500 psi pore fluid pressure would be an overstress condition because the net would be 4,500 psi and that extra 500 psi could irreversibly alter the pore structure in the rock. In another illustration, the overburden fluid pressure may be 9,000 psi while the pore fluid pressure is increased to 6,000 psi, and then the overburden fluid pressure is increased to 10,000 psi, while the net stress is controlled not to exceed 4,000 psi. Yet other variations are also possible.

In one or more examples, the data acquisition system 140 may receive a signal from the overburden fluid pressure gauge 130 and a signal from the pore fluid pressure gauge 132 indicative of respective pressures rather than the pressure transducer making the pressure measurements itself and providing it to the data acquisition system 140. The data acquisition system 140 may filter each signal (e.g., noise filtered and/or oscillation dampened) and calculate a differential pressure based on a difference between these signals which is used to determine whether the core rock sample has reached equilibrium. The overburden fluid pressure gauge 130 and pore fluid pressure gauge 132 may measure the respective pressures at a low resolution. Low resolution may be plus or minus 20 psi or 0.10 percent of the gauge's full scale, for example. This method of determining the differential pressure may be acceptable when a compressive strength of the rock is small because less resolution is needed to measure coarse rock compression effects. Conversely, high resolution pressure measurements are needed to measure fine rock compression effects when a compressive strength of the rock is large. High resolution may be plus or minus 0.50 psi or 0.005 percent of the gauge's full scale. The pressure transducer may be of the "differential" type and measure the overburden fluid pressure and pore fluid pressure directly to achieve the high resolution rather than receiving a respective signal from the overburden fluid pressure gauge 130 and pore fluid pressure gauge 132 indicative of pressures which may be low resolution gauges.

Figure 4:
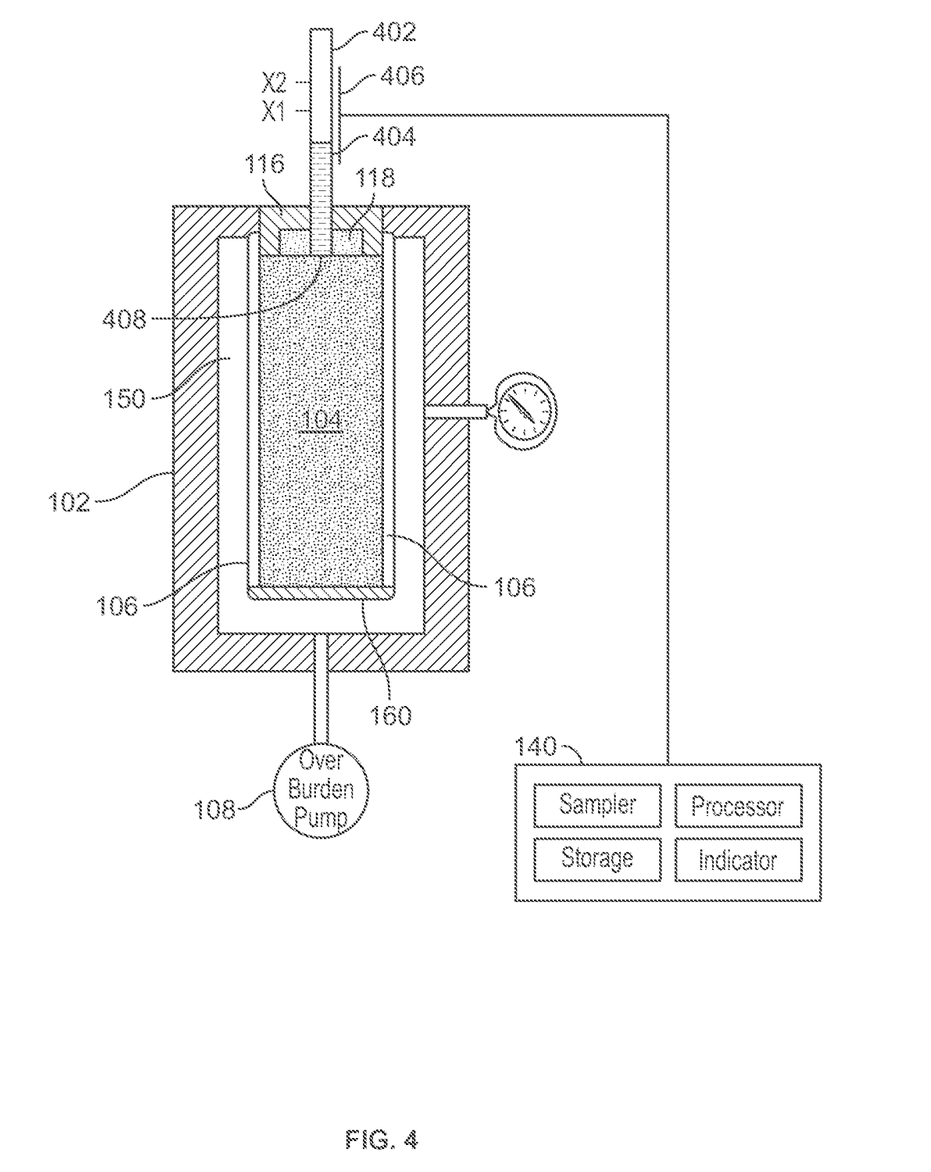
FIG. 4 illustrates another testing arrangement for testing shaped charges prior to being used downhole.

FIG. 4 illustrates another testing chamber 400. The testing chamber 400 can be used to evaluate compression behavior of a core rock sample 104. The testing chamber 400 includes the overburden chamber 102 and a vertically positioned graduated cylinder 402 open to atmospheric pressure. A core rock sample 104 is positioned in a vessel 150 and the overburden pump 108 pumps overburden fluid into the vessel 150. The overburden pump 108 may pump the overburden fluid, e.g., water under pressure, into the vessel 150 and around the sleeve 106 of the core rock sample 104 resulting in the sleeve compressing and squeezing the core rock sample 104 within confines of the vessel 150. An end plate 160 may be positioned at one end of the core rock sample 104 and casing 116 and/or cement 118 may be positioned at another end of the core rock sample 104. In the overburden chamber 102, the sleeve 106 around the core rock sample 104 results in the pore fluid in the core rock sample 104 being pushed through a port 408 at the other end of the core rock sample 104 and into a cylinder such as graduated cylinder 402. A fluid level sensor 406 may provide an indication of the fluid level in the graduated cylinder 402. For example, a level $X_1$ may be a level of pore fluid 404 when the overburden fluid pressure is 1000 psi while a level $X_2$ may be a level of pore fluid 404 when the overburden fluid pressure is 5000 psi. The indication of the fluid level is then provided to the data acquisition system 140 to determine whether the overburden stress on the core rock sample has transferred into and throughout the core rock sample 104. The fluid level sensor 406 may determine the fluid level using different technologies, examples of which include a float, solid-state electro-optical, conductivity, capacitive, ultrasonic, and piezo-resonant.

Figure 5:
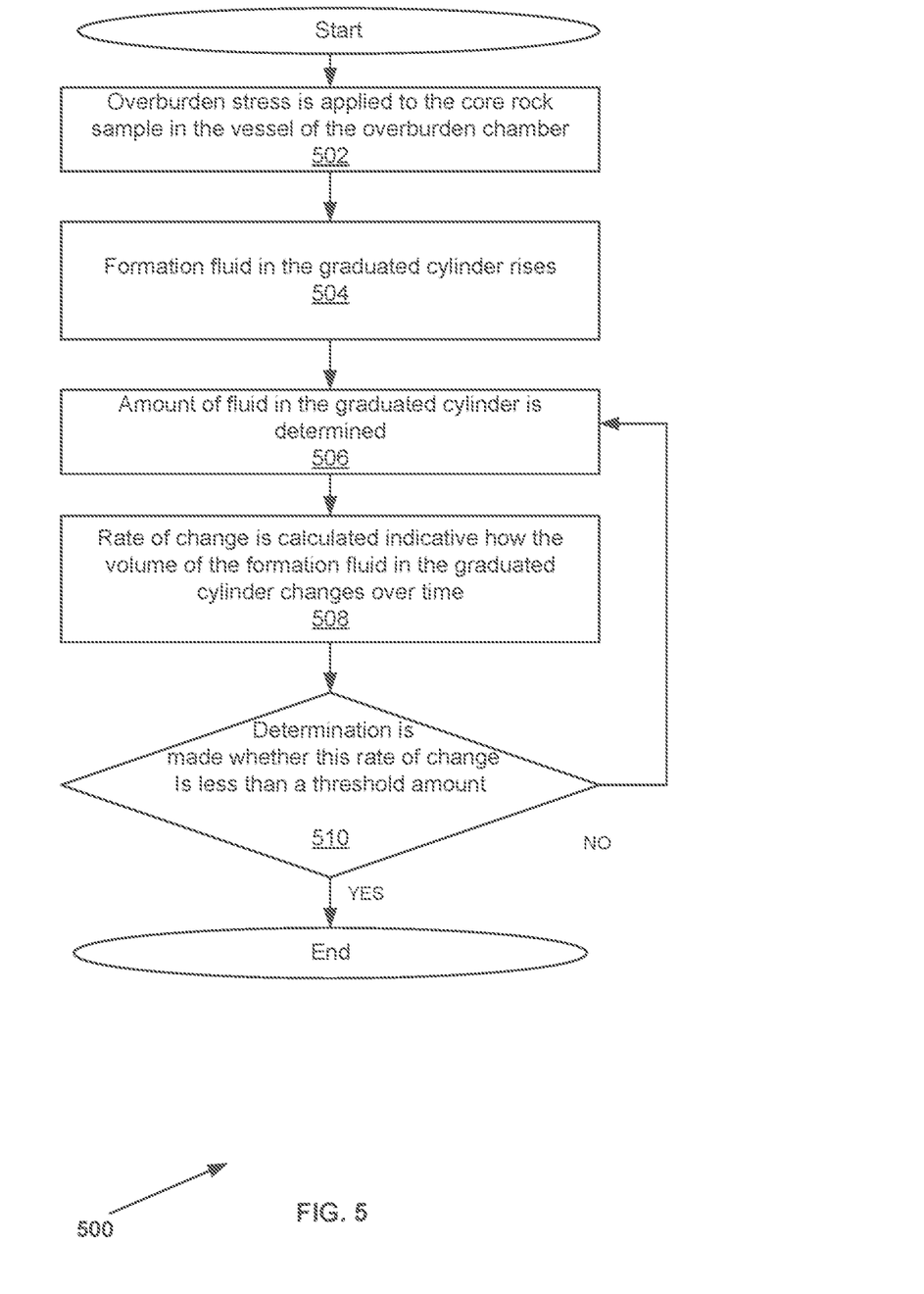
FIG. 5 is another flow chart of functions for determining when applied stress to a core rock sample has equilibrated in the core rock sample.

FIG. 5 is a flow chart 500 of functions associated with the testing chamber 400. A rate of change of the pore fluid in the graduated cylinder is indicative of whether the overburden stress applied on the core rock sample has transferred into and throughout the core rock sample.

At 502, overburden stress is applied on the core rock sample in the vessel of the overburden chamber. The overburden pump may pump the overburden fluid, e.g., water under pressure, into the vessel and around the sleeve of the core rock sample resulting in the sleeve compressing and squeezing the core rock sample within confines of the vessel. At 504, the pore fluid in the graduated cylinder rises. The pore fluid rises based on the overburden stress applied on the core rock sample, pushing the pore fluid in the core rock sample through a port and into the graduated cylinder. At 506, an amount of fluid in the graduated cylinder is determined. For example, the fluid level sensor may provide an indication of a fluid level in the graduated cylinder which is provided to the data acquisition system by the sensor. At 508, a rate of change is calculated indicative how the volume of the pore fluid in the graduated cylinder changes over time. The rate of change may be calculated as a difference of the volume of fluid in the graduated cylinder a time T and the volume of fluid in the graduated cylinder a time T+n, divided by a time interval n. At 510, a determination is made whether the rate of change is less than a threshold amount. If the amount of fluid does not change by the threshold amount, then the stress applied on the core rock sample by the overburden chamber has transferred into and throughout the core rock sample. For example, if a fluid level does not change by 0.002 cc in a given period of time m, the overburden stress applied on the core rock sample has transferred into and throughout the core rock sample. Otherwise, processing returns to 506. The volume of fluid in the graduated cylinder may also be proportional to an amount of compression of the core rock sample.

Figure 6:
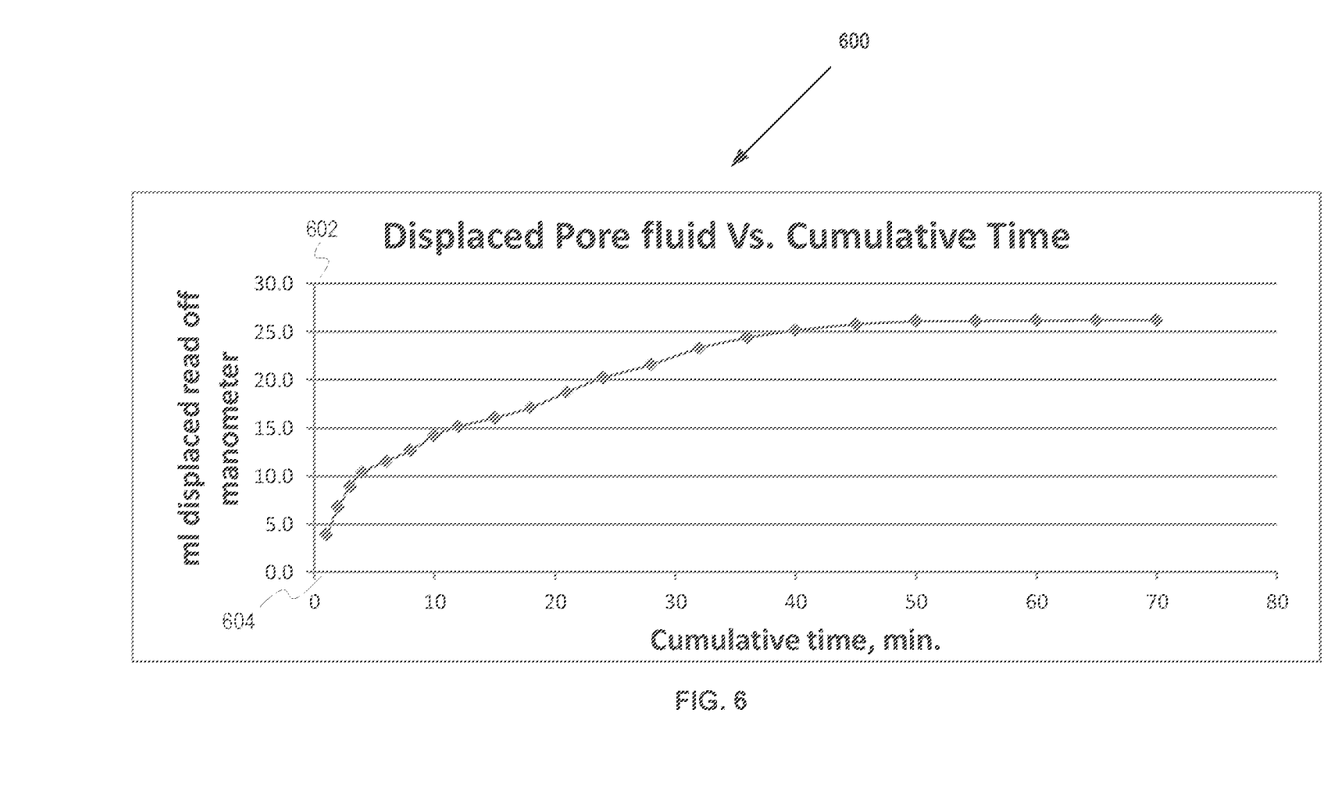
FIG. 6 is an example of a transient pore fluid displacement chart.

FIG. 6 is an example of a transient pore fluid displacement chart 600. The pore fluid displacement chart 600 illustrates how the volume of pore fluid in the graduated cylinder as shown on vertical axis 602 changes over time as shown on horizontal axis 604. When a rate of change of the pore fluid is less than a threshold amount, then the applied stress on the core rock sample has transferred into and throughout the core rock sample.

Testing chamber 400 may guide operation of testing chamber 100. For example, the compression behavior of the core rock sample indicated by the testing chamber 400 can be used to set target pressures associated with testing chamber 100 and/or how determine long it takes for equilibrium to be reached at set target pressures. As another example, time to reach equilibrium as indicated by 100 and 400 may be compared to verify that equilibrium has in fact been reached. As yet another example, a relationship between pore pressure at one atmosphere and compressibility indicated by the testing chamber 400 can be used to estimate compression behavior of the core rock sample at other pore pressures applied in testing chamber 100 and/or how long it takes for equilibrium to be reached at set target pressures. Testing chamber 400 may guide operation of testing chamber 100 in other ways as well.

Figure 7:
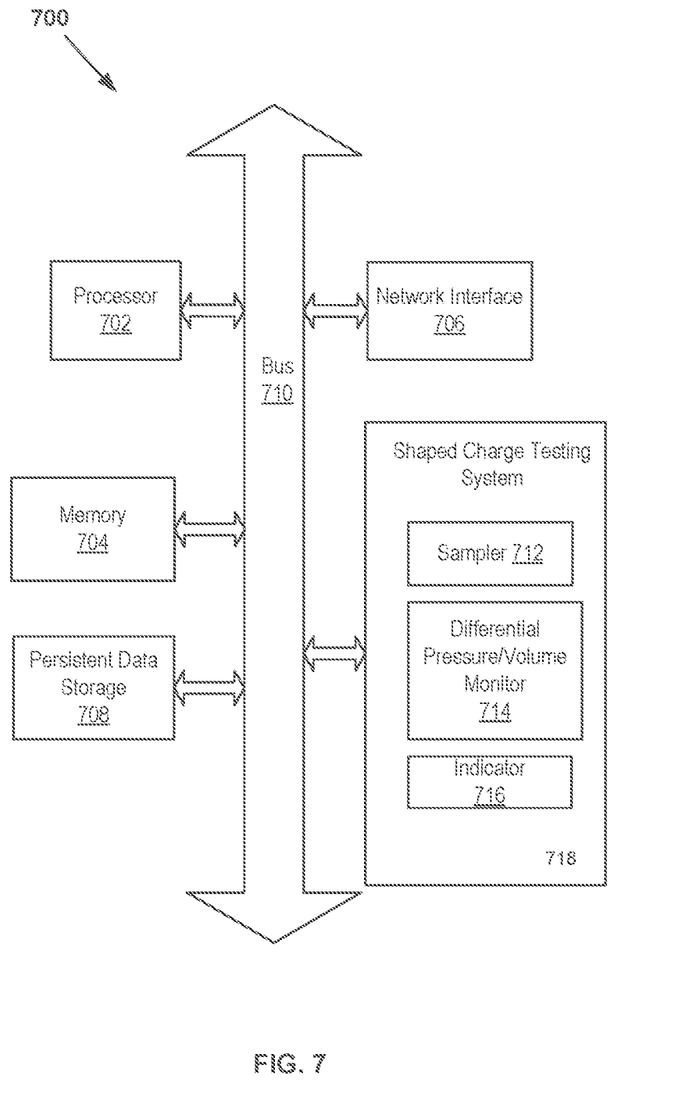
FIG. 7 is a block diagram of apparatus for determining whether applied stress on a core rock sample has equilibrated in the core rock sample.

FIG. 7 is a block diagram of apparatus 700 for determining when stress applied on a core rock sample has transferred into and throughout the core rock sample. The apparatus 700 may be representative of the data acquisition system 140 or some other system associated with determining when applied stress in a core rock sample has equilibrated in the core rock sample in accordance with the functions described herein.

The apparatus 700 includes a processor 702 (possibly including multiple processors, multiple cores, multiple nodes, and/or implementing multi-threading, etc.). The apparatus 700 includes memory 704. The memory 704 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more other possible realizations of non-transitory machine-readable or computer-readable media.

A network interface 706 may be arranged to receive an indication of the differential pressure measurements from the pressure transducer and/or fluid level measurements in the graduated cylinder from the sensor. The persistent data storage 708 can be a hard disk drive, such as a magnetic storage device which stores the measurements over a period of time. The apparatus 700 also includes a bus 710 (e.g., PCI, ISA, PCI-Express).

The apparatus 700 includes a shaped charge testing system 718. The shaped charge testing system 718 includes a sampler 712, a differential pressure/volume monitor 714, and an indicator 716. The sampler 712 may receive one or more of a differential pressure measurement from the differential pressure transducer, an indication of pore fluid pressure from the pore fluid pressure gauge, an indication of overburden fluid pressure from the overburden fluid pressure gauge, and/or a volume measurement of pore fluid in the graduated cylinder at given time intervals. The measurement may be stored in the persistent data storage 708. The differential pressure/volume monitor 714 may calculate a rate of change of differential pressure and/or a volume measurement. When this rate of change is less than a threshold amount, an indicator 716 may generate an audible alert such as a sound and/or visual alert such as a flashing light indicative of the core rock sample equilibrating based on the compression rate. This may indicate that the shaped charge in the perforation gun is to be detonated.

The apparatus 700 may implement any one of the previously described functionalities partially (or entirely) in hardware and/or software (e.g., computer code, program instructions, program code) stored on a machine readable or computer readable medium/media. In some instances, the software is executed by the processor 702. Further, realizations can include fewer or additional components not illustrated in FIG. 7 (e.g., video cards, audio cards, additional network interfaces, peripheral devices, etc.). The processor 702 and the network interface 706 are coupled to the bus 710. Although illustrated as being coupled to the bus 710, the memory 704 can be coupled to the processor 702.

The flowcharts are provided to aid in understanding the illustrations and are not to be used to limit scope of the claims. The flowcharts depict example operations that can vary within the scope of the claims. Additional operations may be performed; fewer operations may be performed; the operations may be performed in parallel; and the operations may be performed in a different order. For example, the operations depicted in blocks 202-214, 502-514 can be performed in parallel or concurrently. It will be understood that each block of the flowchart illustrations and/or block diagrams, and combinations of blocks in the flowchart illustrations and/or block diagrams, can be implemented by program code. The program code may be provided to a processor of a general purpose computer, special purpose computer, or other programmable machine or apparatus.

As will be appreciated, aspects of the disclosure may be embodied as a system, method or program code/instructions stored in one or more non-transitory machine-readable media. Accordingly, aspects may take the form of hardware, software (including firmware, resident software, microcode, etc.), or a combination of software and hardware aspects that may all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine readable medium(s) may be utilized. The machine readable medium may be a machine readable signal medium or a machine readable storage medium. A machine readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine readable storage medium may be any tangible medium that can contain, or store a program for use by or in connection with an instruction execution system, apparatus, or device. A machine readable storage medium is not a machine readable signal medium.

A machine readable signal medium may include a propagated data signal with machine readable program code embodied therein, for example, in baseband or as part of a carrier wave. Such a propagated signal may take any of a variety of forms, including, but not limited to, electromagnetic, optical, or any suitable combination thereof. A machine readable signal medium may be any machine readable medium that is not a machine readable storage medium and that can communicate, propagate, or transport a program for use by or in connection with an instruction execution system, apparatus, or device.

Program code embodied on a machine readable medium may be transmitted using any appropriate medium, including but not limited to wireless, wireline, optical fiber cable, RF, etc., or any suitable combination of the foregoing.

Computer program code for carrying out operations for aspects of the disclosure may be written in any combination of one or more programming languages, including an object oriented programming language such as the Java® programming language, C++ or the like; a dynamic programming language such as Python; a scripting language such as Perl programming language or PowerShell script language; and conventional procedural programming languages, such as the "C" programming language or similar programming languages. The program code may execute entirely on a stand-alone machine, may execute in a distributed manner across multiple machines, and may execute on one machine while providing results and or accepting input on another machine.

The program code/instructions may also be stored in a machine readable medium that can direct a machine to function in a particular manner, such that the instructions stored in the machine readable medium produce an article of manufacture including instructions which implement the function/act specified in the flowchart and/or block diagram block or blocks.

While the aspects of the disclosure are described with reference to various implementations and exploitations, it will be understood that these aspects are illustrative and that the scope of the claims is not limited to them. In general, techniques for determining when applied stress on a core rock sample has equilibrated in the core rock sample as described herein may be implemented with facilities consistent with any hardware system or hardware systems. Many variations, modifications, additions, and improvements are possible.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the disclosure. In general, structures and functionality presented as separate components in the example configurations may be implemented as a combined structure or component. Similarly, structures and functionality presented as a single component may be implemented as separate components. These and other variations, modifications, additions, and improvements may fall within the scope of the disclosure.

Use of the phrase "at least one of" preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed.

Example Embodiments

Example embodiments include the following:

Embodiment 1: A method comprising: applying overburden stress on a core rock sample positioned in a sleeve and pore pressure in the core rock sample; measuring an overburden fluid pressure indicative of the overburden stress and a pore fluid pressure indicative of the pore pressure; determining a difference between the overburden fluid pressure and pore fluid pressure; repeating the measuring and determination of the difference over a period of time; determining a rate of change of the difference over the period of time; and outputting an indication of the rate of change meeting a threshold level indicative of the overburden stress transferring into and throughout the core rock sample.

Embodiment 2: The method of Embodiment 1, wherein outputting the indication comprises providing an audible or visual indication of the rate of change meeting the threshold level.

Embodiment 3: The method of Embodiment 1 or 2, further comprising detonating a shaped charge based on the output of the indication.

Embodiment 4: The method of any one of Embodiments 1-3, wherein determining the rate of change comprises subtracting respective differences determined at time T and T+t.

Embodiment 5: The method of any one of Embodiments 1-4, wherein applying overburden stress and pore fluid pressure comprises pumping overburden fluid into a vessel of the overburden chamber which contains the core rock sample until an overburden fluid pressure meets a first target value and pumping the pore fluid until the pore fluid pressure meets a second target value.

Embodiment 6: The method of any one of Embodiments 1-5, wherein the first target value 10,000 pounds per square inch (psi) and the second target value is 8,000 psi.

Embodiment 7: The method of any one of Embodiments 1-6, wherein determining the difference between the overburden fluid pressure and pore fluid pressure comprise sampling the overburden fluid pressure and the pore fluid pressure at a given time interval.

Embodiment 8: Apparatus comprising: an overburden chamber comprising overburden pressure fluid, a vessel, a core rock sample in the vessel, and a sleeve positioned around the core rock sample, wherein the core rock sample is saturated with a pore fluid; a pressure transducer coupled to tubing with the overburden pressure fluid and tubing with the pore fluid, wherein the differential pressure gauge outputs a difference between an overburden fluid pressure and pore fluid pressure; an indicator arranged to provide an indication that the overburden stress is transferred into and throughout the core rock sample based on the difference.

Embodiment 9: The apparatus of Embodiment 8, wherein the pressure transducer further comprises a sampler arranged to sample the overburden fluid pressure and pore fluid pressure.

Embodiment 10: The apparatus of Embodiment 8 or 9, wherein the pressure transducer is arranged to determine a rate of change of the difference at successive time intervals.

Embodiment 11: The apparatus of any one of Embodiments 8-10, further comprising an indicator arranged to provide a visual or audible indicator when the rate of change is below a threshold level.

Embodiment 12: The apparatus of any one of Embodiments 8-11, further comprising a wellbore chamber comprising a perforation gun having a shaped charge, wherein the shaped charge is detonated when the rate of change is less than a threshold amount.

Embodiment 13: The apparatus of any one of Embodiments 8-12, wherein the core rock sample is Indiana sandstone or Berea sandstone and the pore fluid is kerosene, lab oil, mineral oil, or brine.

Embodiment 14: The apparatus of any one of Embodiments 8-13, further comprising a first pump arranged to pump the overburden fluid to a first target pressure in the vessel and a second pump arranged to pump the pore fluid to a second target pressure and then stopping the pumping by the first pump and second pump.

Embodiment 15: A non-transitory machine-readable medium containing program instructions executable by a processor to perform the functions of:
applying overburden stress on a core rock sample positioned in a sleeve and pore pressure in the core rock sample; measuring an overburden fluid pressure indicative of the overburden stress and a pore fluid pressure indicative of the pore pressure; determining a difference between the overburden fluid pressure and pore fluid pressure; repeating the measuring and determination of the difference over a period of time; determining a rate of change of the difference over the period of time; and outputting an indication of the rate of change meeting a threshold level indicative of the overburden stress transferring into and throughout the core rock sample.

Embodiment 16: The non-transitory machine-readable medium of Embodiment 15, wherein the program instructions for outputting the indication comprises program instructions for providing an audible or visual indication of the rate of change meeting a threshold level.

Embodiment 17: The non-transitory machine-readable medium of Embodiment 15 or 16, further comprising program instructions for detonating a shaped charge in a perforation gun based on the indication.

Embodiment 18: The non-transitory machine-readable medium of any one of Embodiments 15-17, wherein the program instructions for determining the rate of change comprises program instructions for subtracting differences determined at time T and T+t.

Embodiment 19: The non-transitory machine-readable medium of any one of Embodiments 15-18, wherein the first target value 10,000 psi and the second target value is 8,000 psi.

Embodiment 20: The non-transitory machine-readable medium of any one of Embodiments 15-19, wherein the program instructions for determining the difference between the overburden fluid pressure and pore fluid pressure comprises program instructions to sample the overburden fluid pressure and pore fluid pressure.

What is claimed is:
1. A method comprising:
applying overburden stress on a core rock sample positioned in a sleeve and pore pressure in the core rock sample;
measuring an overburden fluid pressure indicative of the overburden stress and measuring a pore fluid pressure indicative of the pore pressure;
determining a pressure difference between the overburden fluid pressure and pore fluid pressure;
repeating the measuring and determination of the pressure difference over a period of time;
determining a rate of change of the pressure difference over the period of time;
outputting an indication of the rate of change of the pressure difference meeting a threshold level indicative of the overburden stress transferring into and throughout the core rock sample;
while maintaining the pressure difference, detonating a shaped charge positioned adjacent to the core rock sample based on the outputting of the indication that the rate of change has met the threshold level, and performing an evaluation of perforations formed in the core rock sample created by the detonation of the shaped charge.

2. The method of claim 1, wherein outputting the indication comprises providing an audible or visual indication of the rate of change meeting the threshold level.

3. The method of claim 1, wherein determining the rate of change comprises subtracting respective differences determined at time T and T+t.

4. The method of claim 1, wherein applying overburden stress and pore fluid pressure comprises pumping overburden fluid into a vessel of an overburden chamber which contains the core rock sample until an overburden fluid pressure meets a first target value and pumping the pore fluid until the pore fluid pressure meets a second target value.

5. The method of claim 4, wherein the first target value 10,000 pounds per square inch (psi) and the second target value is 8,000 psi.

6. The method of claim 1, wherein determining the pressure difference between the overburden fluid pressure and pore fluid pressure comprise sampling the overburden fluid pressure and the pore fluid pressure at a given time interval.

7. An apparatus comprising:
   an overburden chamber comprising overburden pressure fluid, a vessel, a core rock sample in the vessel, and a sleeve positioned around the core rock sample, wherein the core rock sample is saturated with a pore fluid;
   a pressure transducer coupled to tubing with the overburden pressure fluid and tubing with the pore fluid, wherein a differential pressure gauge outputs an indication of a pressure difference between an overburden fluid pressure and pore fluid pressure;
   an indicator arranged to provide an indication that the overburden stress is transferred into and throughout the core rock sample based on the pressure difference; and
   a perforation gun positioned within the vessel and including a shaped charge, the perforation gun configured to detonate the shaped charged based on the indication of the pressure difference between the overburden fluid pressure and the pore fluid pressure, the shaped charge configured to form one or more perforations within the core rock sample.

8. The apparatus of claim 7, wherein the pressure transducer further comprises a sampler arranged to sample the overburden fluid pressure and pore fluid pressure.

9. The apparatus of claim 7, wherein the pressure transducer is arranged to determine a rate of change of the pressure difference at successive time intervals.

10. The apparatus of claim 9, wherein the indicator is arranged to provide a visual indication or an audible indication when the rate of change is below a threshold level.

11. The apparatus of claim 10, wherein the shaped charge is detonated when the rate of change is less than a threshold amount.

12. The apparatus of claim 7, wherein the core rock sample is Indiana sandstone or Berea sandstone and the pore fluid is kerosene, lab oil, mineral oil, or brine.

13. The apparatus of claim 7, further comprising a first pump arranged to pump the overburden fluid to a first target pressure in the vessel and a second pump arranged to pump the pore fluid to a second target pressure and then stopping the pumping by the first pump and second pump.

14. A non-transitory machine-readable medium containing program instructions executable by a processor to perform the functions of:
   applying overburden stress on a core rock sample positioned in a sleeve and pore pressure in the core rock sample;
   measuring an overburden fluid pressure indicative of the overburden stress and measuring a pore fluid pressure indicative of the pore pressure;
   determining a pressure difference between the overburden fluid pressure and pore fluid pressure;
   repeating the measuring and determination of the pressure difference over a period of time;
   determining a rate of change of the pressure difference over the period of time;
   outputting an indication of the rate of change meeting a threshold level indicative of the overburden stress transferring into and throughout the core rock sample; and
   while maintaining the pressure difference, detonating a shaped charge positioned adjacent to the core rock sample based on the outputting of the indication that the rate of change has met the threshold level.

15. The non-transitory machine-readable medium of claim 14, wherein the program instructions for outputting the indication comprises program instructions for providing an audible or visual indication of the rate of change meeting a threshold level.

16. The non-transitory machine-readable medium of claim 14, wherein the program instructions for determining the rate of change comprises program instructions for subtracting differences determined at time T and T+t.

17. The non-transitory machine-readable medium of claim 14,
   wherein applying overburden stress and pore fluid pressure comprises pumping overburden fluid into a vessel of an overburden chamber which contains the core rock sample until an overburden fluid pressure meets a first target value and pumping the pore fluid until the pore fluid pressure meets a second target value, and
   wherein the first target value 10,000 psi and the second target value is 8,000 psi.

18. The non-transitory machine-readable medium of claim 14, wherein the program instructions for determining the pressure difference between the overburden fluid pressure and pore fluid pressure comprises program instructions to sample the overburden fluid pressure and pore fluid pressure.

* * * * *